United States Patent [19]

Winchell

[11] 4,093,169

[45] June 6, 1978

[54] ATTACHABLE HANGER FOR CONTAINERS

[75] Inventor: David A. Winchell, Twin Lakes, Wis.

[73] Assignee: Baxter Travenol Laboratories, Inc., Deerfield, Ill.

[21] Appl. No.: 752,643

[22] Filed: Dec. 20, 1976

[51] Int. Cl.² .............................................. B65D 23/10
[52] U.S. Cl. ............................. 248/311.3; 215/100 A; 248/318; 248/359
[58] Field of Search ............... 248/318, 317, 359, 360, 248/311.3; 215/100 A; 222/181; D9/10, 163

[56] References Cited

U.S. PATENT DOCUMENTS

| 757,638 | 4/1904 | Roake | 248/359 |
|---|---|---|---|
| 3,137,423 | 6/1964 | Tupper | 215/100 A |
| 3,199,737 | 8/1965 | Koffler | 248/359 |
| 3,381,838 | 5/1968 | McClain et al. | 215/100 R |
| 3,441,172 | 4/1969 | Dike | 215/100 A |
| 3,484,070 | 12/1969 | Horodko et al. | 248/317 |
| 3,581,928 | 6/1971 | Amand | 215/100 A |
| 3,717,277 | 2/1973 | Stengle | 215/100 A |
| 3,865,339 | 2/1975 | Von Alven | 248/318 |
| 3,880,312 | 4/1975 | Gilbert | 248/359 |
| 4,010,862 | 3/1977 | Gilbert | 215/100 A |

FOREIGN PATENT DOCUMENTS 2,310,956  9/1974  Germany ............................ 248/359

Primary Examiner—Marion Parsons, Jr.
Attorney, Agent, or Firm—Paul C. Flattery; John P. Kirby, Jr.; Gary W. McFarron

[57] ABSTRACT

A one-piece hanger for a container comprises attachment means to a container and an elongated, flexible hanger member secured at both ends to the attaching means to define a closed loop. The elongated hanger member is positioned in generally longitudinal relationship to the attaching means and defines a pair of first flex sections positioned respectively adjacent the ends of the hanger members, and a pair of spaced second flex sections positioned more remotely from the ends of the flexible hanger member. Accordingly, the hanger member is generally approximately coplanar with the attachment means so that it does not project upwardly away from the container which carries it. However, the hanger can be bent into transverse relation to the attachment means to unfold and expose a large loop for hanging of the container.

8 Claims, 5 Drawing Figures

ATTACHABLE HANGER FOR CONTAINERS

BACKGROUND OF THE INVENTION

This application relates to a hanger for containers and the like which may be made of a single piece of plastic and which, if desired, may be made separate from the container, for attachment to various container units when and as desired. Alternatively, the hanger may be made integral with a plastic container.

Sterile medical solution containers are usually provided with a hanger at the bottom of the container, so that they can be hung from an inverted position for administration of the medical liquids, such as parenteral solutions, wash solutions, or the like. Examples of patents which show such hangers include Betka U.S. Pat. No. D-235,310, Fujio U.S. Pat. No. 3,744,658, and Von Alvan U.S. Pat. No. 3,865,339.

The hanger of this invention makes use of a unique combination of features to provide significant advantages of construction and operation over the prior art.

For example, the hanger of this invention may be simply snapped onto the tail pinch seal of a blow molded plastic bottle, which permits application to a plastic bottle in which the entire tail seal is recessed. This is advantageous over the design, for example, of U.S. Pat. No. D-235,310, in which the hanger slides onto the end of the tail seal, rather than snapping on, and permits use of the hanger of this invention with a more easily molded, recessed tail seal as illustrated in the drawings of this application.

Additionally, the hanger of this invention can be completely recessed into the bottom of the bottle, in its initial configuration, when used in conjunction with a bottle defining a recessed tail seal.

The hanger of this invention is attached with flexible joints instead of folding hinges. This aids in the manufacture of the hanger in that (1) the plastic does not have to flow through a very thin section of the mold cavity to fill the entire cavity, and (2) molded hinges require immediate flexing after molding to ensure their strength and flexibility while being used, while the thicker flexible joints of this invention do not require such working.

While the hanger of this invention can lie in the recessed portion of a bottle and so as not to interfere with the standing up of the bottle, it unfolds to form an extra-large loop for facilitating ease of hanging. This is because of the initial, folded configuration of the hanger of this invention, which can unfold to form the extra-large loop.

DESCRIPTION OF THE INVENTION

In accordance with this invention, a one-piece hanger for a container is provided which comprises means for attaching the hanger member to a container. An elongated, flexible hanger member, generally made out of plastic, is secured at both ends thereof to the attaching means, so that the elongated hanger member defines a closed loop. The hanger member is positioned in generally longitudinal relationship to the hanger means. That is to say: the plane of the elongated hanger member is generally parallel to the axis of the attachment means, which is usually an elongated gripper structure or the like. However, it is also contemplated that the elongated hanger member may be formed at a small angle of five degrees or so to the attachment means, inclining in the direction of the container carrying the hanger means, so that the elongated hanger member is slightly biased to press against the container when the attachment means is mounted thereon. This causes the elongated hanger member to remain out of the way in an end recess of the container, so the container may stand up until the hanger is extended by the fingers for use. This slight angular relationship to the attaching means is considered to be included within the scope of a "generally longitudinal relation."

The elongated hanger member defines a pair of first flex sections positioned respectively adjacent the ends of the hanger member where the connection is made with the attaching means. The first flex sections are adapted to bend, to permit the hanger member to be pulled into a more transverse relationship with the attaching means by the fingers, so that the loop defined by the elongated hanger member may be used for hanging the container on a hook or the like.

The elongated hanger member also defines a pair of spaced, second flex sections positioned in spaced relation with the ends of the elongated hanger member. The second flex sections are also adapted to bend, which further facilitates the unfolding of the elongated hanger member into the more transverse relationship with the attachment means.

Typically, the portion of the elongated, flexible hanger member between the second flex sections is generally U-shaped. The second flex sections are shaped to define arcs of an angle sufficient to direct and position the first flex sections and the attaching means into a position which is within the U-shaped portion.

Preferably, the first flex sections protrude transversely from the attaching means, and further define an essentially 90° turn, to connect with straight portions of the elongated hanger member, which are respectively positioned between first and second flex sections, so that the first flex sections and the straight portions defined above define a second, generally U-shaped configuration, with the attachment means bisecting the second U-shaped configuration.

Generally, when the elongated hanger member is unfolded and extended into transverse relationship with the attachment means, for hanging of the container, the plane of the loop defined by the elongated hanger member is also transverse to the axis of the hanger member, rather than being generally parallel thereto, as is the case in U.S. Pat. No. D-235,310. This facilitates the nesting of the folded hanger within a recessed area of a blow-molded container as shown in the drawing.

In the drawings, FIG. 1 is a bottom plan view of one embodiment of the hanger of this invention.

Figure 1:
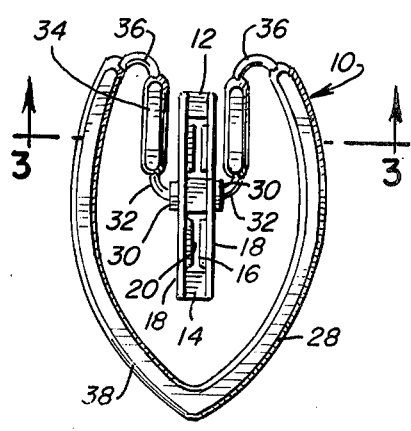
Figures 3, 4:
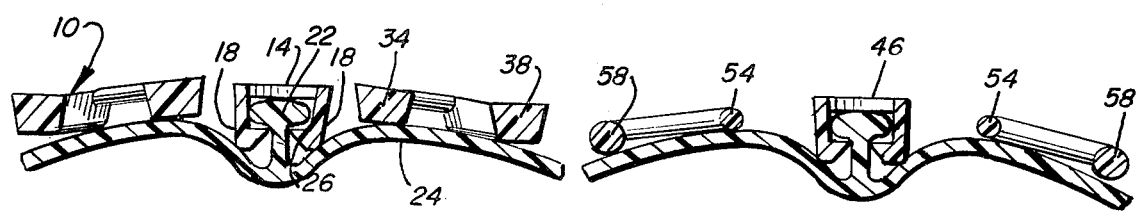
FIG. 3 is a sectional view taken along line 3—3 of FIG. 1, showing the hanger of this invention being attached to a tail or end seal of a blow molded plastic container.
FIG. 4 is a sectional view taken along line 4—4 of FIG. 2, also showing the hanger being attached in a manner similar to FIG. 3 to a blow molded plastic container.
Figure 5:
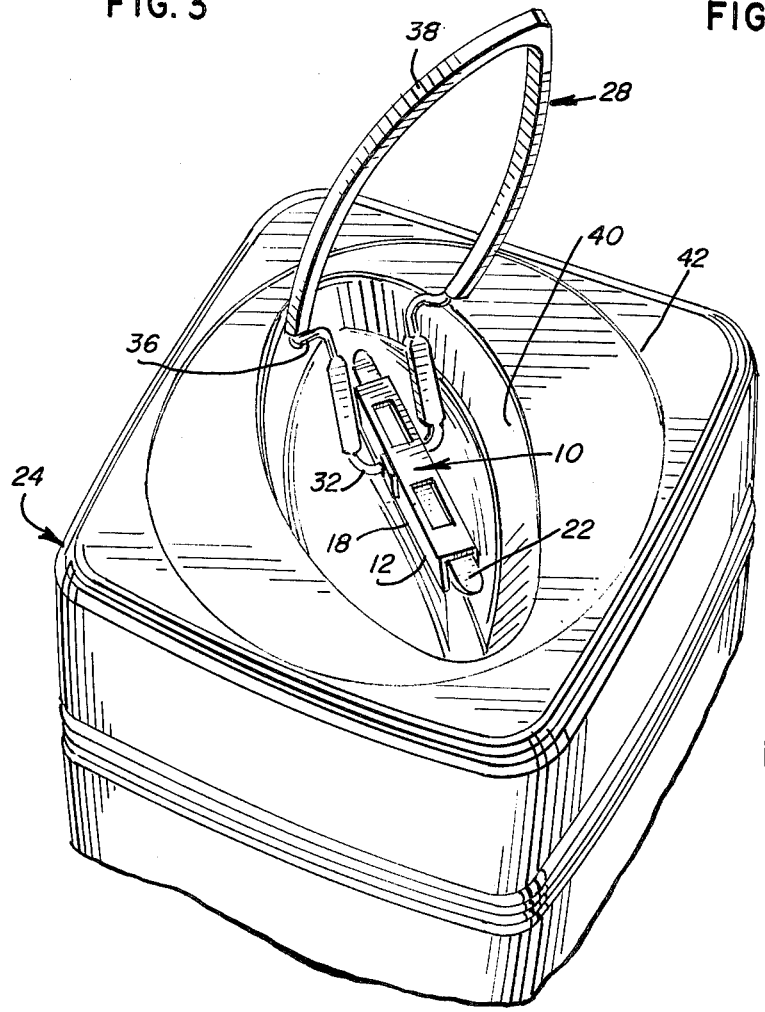
FIG. 5 is a perspective view of the end of an inverted, blow molded plastic container, showing the hanger of FIG. 1 attached thereto and being partially unfolded and extended into transverse relationship.

Referring to FIGS. 1, 3, and 5, hanger 10 is shown made of an integrally molded piece of nylon thermoplastic, polypropylene, or the like, and including means 12 for attaching the hanger member to a container.

Attachment means 12 is an elongated structure defining a top wall 14 containing apertures 16, and a pair of opposed side walls 18.

Side walls 18 define gripper members 20, which can grasp the bulbous tail seal 22 of a blow-molded plastic container 24, for retention of hanger 10.

Attachment means 12 may be snapped onto tail seal 22 by the spreading and camming action of beveled surfaces 26 of gripper members 20.

Elongated, flexible hanger member 28 is attached at both ends 30 to the attaching means 12, generally at the respective side walls 18.

Figure 2:
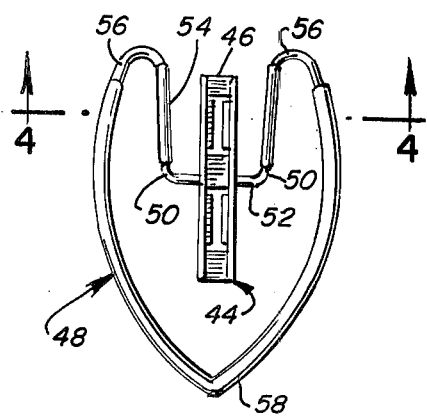
FIG. 2 is a bottom plan view of another embodiment of the hanger of this invention.

A pair of first flex sections 32 are positioned respectively adjacent the ends 30 to the hanger member. Flex sections 32 may be defined by a thinner portion of the elongated hanger member 28 as shown in FIG. 1, or they may also be defined by curving sections 50 of the hanger member as shown in FIG. 2.

Straight portions 34 separate first flex sections 32 from second flex sections 36, which define arc-sections which may be, if desired, of smaller transverse dimension than the bulk of hanger member 28.

Second flex sections 36 may be separated by a generally U-shaped portion 38 of hanger member 28, with the second flex sections 36 defining arcs, preferably of about 140° to 180°, and of an angle sufficient to direct first flex sections 32 and the attaching means 12 into a position which is within the U-shaped portion 38, as shown in FIG. 1. Thus, the hanger exhibits a folded configuration in which straight portions 34 are reversely folded into U-shaped portion 38, to reduce the size of hanger member when compared with the aperture size which can be formed by the loop of hanger member 10.

As shown in FIG. 3, the attached hanger 10 can lie flat against the bottom of the container. In particular, hanger 10 can be proportioned to fit within a recess 40 which may be formed as part of a tail seal of container 24, so that container 24 may stand upon its lower end 42 without interference from hanger 10.

When it is desired to use the hanger, portion 38 may be grasped with the fingers and pulled outwardly, so that the loop-like hanger member 28 is pulled out of recess 40 and into transverse relation with attachment means 12. As this happens, pivoting and bending takes place at first flex sections 32 and second flex sections 36, to unfold the elongated hanger member 28 into a loop which is relatively enlarged over conventional unfolded hanger loops, to facilitate the easy hanging of the container.

FIGS. 2 and 4 illustrate another hanger 44 which is generally similar in concept and operation to hanger 10. Attachment means 46 is similar in operation and function to that of the previous embodiment. Elongated hanger member 48 is attached at its ends to the attachment means 46 as in the previous embodiment. First flex sections 50 are primarily defined by the abrupt angle at flex section 50, and serve primarily to provide rotational flexing. Flex sections 50 are also spaced slightly by sections 52 from attachment means 46. In operation, straight sections 54 tend not to flex, although they are only slightly larger, if at all, than flex sections 50.

Second flex sections 56 once again define arcs for flexing in a manner analogous to that shown in FIGS. 1 and 5. Second flex sections 56 once again define arcs of curvature similar to second flex sections 36, to direct first flex sections 50 and attachment member 46 to a position within the U-shaped portion 58 of elongated hanger member 48.

Accordingly, the hanger of this invention provides a folded structure which can unfold into an extra-large loop for hanging, while at the same time remaining out of the way until such time as it is needed.

The above has been offered for illustrative purposes only, and is not for the purpose of limiting the application of this invention, which is as defined in the claims below.

That which is claimed is:

1. A one-piece hanger for a container which comprises:
    means for attaching said hanger member to a container, an elongated, flexible hanger member, secured at both ends thereof to said attaching means to define a closed loop, and positioned in generally coplanar relationship to said attaching means, said elongated hanger member defining a pair of first flex sections positioned respectively adjacent the ends of said hanger member said first flex sections being adapted to bend to permit said hanger member to be pulled into a more transverse relationship with said attaching means, said elongated hanger member also defining a pair of curved, spaced, second flex sections positioned in spaced relation with the ends of said elongated flexible hanger member, said second flex sections being also adapted to bend, to facilitate the moving of said elongated hanger member into said more transverse relationship.

2. The hanger of claim 1 in which the portion of said elongated, flexible hanger member between said second flex sections is of generally U-shaped configuration, said second flex sections defining arcs of an angle sufficient to direct said first flex sections and said attaching means into a position which is within said U-shaped portion.

3. The one-piece hanger of claim 2 in which the portion of said hanger member defining said first and second flex sections is of reduced transverse dimension when compared with the remainder of said hanger member.

4. A one-piece hanger for a container which comprises:
    means for attaching said hanger member to a container, an elongated flexible hanger member, secured at both ends thereof to said attaching means to define a closed loop, and positioned in generally longitudinal relationship to said attaching means, said elongated hanger member defining a generally U-shaped-relatively rigid portion, second flex sections, attached at the ends of said U-shaped portion, said second flex sections defining arcs of an angle sufficient to direct the ends of said elongated flexible hanger member, and said attaching means, into a position which is within said U-shaped portion, and a pair of first, flex sections positioned adjacent the ends of said elongated hanger member to facilitate the moving of said elongated hanger member into a more transverse relationship with said attaching means while unfolding about said first and second flex sections.

5. The one-piece hanger of claim 4 in which the portion of said hanger member defining said first and second flex sections is of reduced transverse dimension when compared with the remainder of said hanger member.

6. The hanger of claim 4 in which said first flex sections protrude transversely from said attaching means and further define an essentially 90° turn to connect with straight portions of said hanger member positioned between said first and second flex sections.

7. The hanger of claim 6 in which said attaching means comprises a pair of parallel walls defining an open bottom, and gripper members carried by the inside of said parallel walls to grasp a projection on a container positioned between said walls, for retention of the hanger on the container.

8. The hanger of claim 7, attached to an end seal of a blow molded plastic solution container.

* * * * *